(12) United States Patent
Choi et al.

(10) Patent No.: US 6,893,614 B2
(45) Date of Patent: May 17, 2005

(54) REACTION DEVICE FOR ORGANIC SYNTHESIS

(75) Inventors: Ho-Il Choi, Taejon (KR); Seung-Gu Chang, Taejon (KR); Sun-Young Kim, Taejon (KR); Seong-Kyu Kim, Taejon (KR); Jeong-Kyu Bang, Taejon (KR)

(73) Assignee: Peptron Inc, Taejon (KR)

(*) Notice: Subject to any disclaimer, the term of this patent is extended or adjusted under 35 U.S.C. 154(b) by 431 days.

(21) Appl. No.: 09/980,050

(22) PCT Filed: Feb. 16, 2001

(86) PCT No.: PCT/KR01/00232

§ 371 (c)(1),
(2), (4) Date: Mar. 13, 2002

(87) PCT Pub. No.: WO01/72411

PCT Pub. Date: Oct. 4, 2001

(65) Prior Publication Data

US 2003/0026745 A1 Feb. 6, 2003

(30) Foreign Application Priority Data

Mar. 29, 2000 (KR) ......................................... 2000-16267

(51) Int. Cl.⁷ ............................. B01L 11/00; C07K 1/04
(52) U.S. Cl. ................. 422/131; 435/287.2; 435/288.3; 530/334

(58) Field of Search ................................. 422/131, 101, 422/102, 103, 104; 435/287.2, 288.3, 305.3; 530/334

(56) References Cited

U.S. PATENT DOCUMENTS

| | | | |
|---|---|---|---|
| 5,053,454 A | 10/1991 | Judd | 525/54.11 |
| 5,240,680 A | 8/1993 | Zuckermann et al. | 422/67 |
| 5,609,826 A | 3/1997 | Cargill et al. | 422/99 |
| 5,762,881 A | 6/1998 | Harness et al. | 422/132 |
| 6,309,608 B1 * | 10/2001 | Zhou et al. | 422/131 |

FOREIGN PATENT DOCUMENTS

| | | |
|---|---|---|
| EP | 529504 A | 3/1993 |
| KR | 95-10946 A | 5/1995 |

* cited by examiner

*Primary Examiner*—N. Bhat
(74) *Attorney, Agent, or Firm*—Lloyd W. Sadler

(57) ABSTRACT

The present invention relates to a reaction vessel for organic synthesis and a block device for the reaction vessel and synthetic method of compound using thereof. More particularly, the present invention provides a solid phase synthetic reaction vessel and a block device for the reaction vessels which are capable of simultaneously synthesizing chemical libraries by combinatorial chemistry method automatically or semiautomatically.

7 Claims, 5 Drawing Sheets

REACTION DEVICE FOR ORGANIC SYNTHESIS

TECHNICAL FIELD OF INVENTION

The present invention relates to a reaction vessel for organic synthesis and a block device for reaction vessels. In particular, the present invention provides, in generating combinatorial libraries of chemical compounds, a economical and universally usable reaction vessel and a block device mountable the same which can automatically or semiautomatically perform multiple solid phase reactions for the synthesis of organic compounds.

BACKGROUND ARTS

Current trends in the development of new drugs are focused on the method combinatorial chemistry which allows to simultaneously synthesize tens of thousands of chemical compounds and then screen their biological activities at a time. Currently, the combinatorial chemistry is the most effective method in the discovery process of lead compounds for new drugs or in the discovery process of new drug candidates having high biological activities among derivatives of lead compounds.

Combinatorial chemistry has been rapidly advanced since the solid phase reaction was made possible by the development of Merrifield resin in 1963, while previously chemical reactions were conducted only in the liquid phase. Subsequent development of new solid phase resins by many researchers, for example Wang etc. has spurred further advances in the field of solid phase chemical reactions. In early days solid phase synthesis was concentrated on the synthesis of peptides and oligonucleotides, and then is used as universal and the most effective way to generate libraries of chemical compounds. For the solid phase synthesis, it may be possible to remove solvents and reagents used in excess by a simply filtering the final products as well as to simultaneously synthesize large numbers of molecules and thereby much more rapidly and easily synthesize large numbers of molecules than the conventional liquid phase reactions.

According to the above mentioned advantages of the solid phase reactions, the combinatorial chemistry may allow to rapidly and easily generate libraries of chemical compounds that may vary in their chemical structures, by repeatedly and systematically combining components having various chemical structures and thereby using minimum time and efforts in the synthesis of new compounds.

Solid phase synthesis was firstly used in the synthesis of peptides in the 1960s, and then applied in the synthesis of non-peptides in the 1970s, and finally a group of compounds composed of peptides has been made for the first time in the 1980s, while the development of appropriate synthetic apparatuses suitable for combinatorial chemistry was insufficient. Synthetic technologies suitable for the concept of combinatorial chemistry in the discovery process of new drugs have been started to develop in the 1990s, and subsequently, the necessary synthetic apparatuses have been started to develop.

As above mentioned, the technologies of combinatorial chemistry advance steadily, but the technologies in Korea related to syntheses and apparatuses remains to be developed as it is still new area.

Generally, for a reaction vessel used to construct groups of chemical compounds by solid phase synthesis method, a microtiter well plate having a plurality of wells or a vessel in the form of an injection syringe is used. For an instance, the most recently produced organic synthetic apparatus from FlexChem Corp. has adopted a box having 96 wells as a synthetic vessel and the apparatus was devised that the chemical reactions are conducted within the every respective well. However, it is very difficult to observe the reaction phenomena taking place in each well during reaction, and also practically impossible to confirm the chemical process in each and all of the 96 wells. Further, the reaction vessels where resin is laminated in the vertical direction demand a considerable time to set the initial reaction apparatus, and it is hard to secure the airtightness of the filter during the reaction.

For another example, the synthetic apparatus produced by Advanced ChemTech Corp. has also adopted vertical style for the reaction vessels and so it has similar problems as above FlexChem Corp's.

Further, automatic or semiautomatic synthetic apparatuses produced by Chiron Corp., Bodhan Automation, Inc., and Ontogen Corp. has also of vertical styles, and are inconvenient in that each requires an installment of specific gaskets. Moreover, in such reaction devices comprising many reaction vessels as the above it is difficult to oversee each and all the phenomena occurring during the reaction in all those vessels, and also because it is improper to use the very same reaction conditions for all syntheses of new substances at all times it follows that all organic synthesis conditions do not always fit to these automatic apparatuses, posing a serious problem Ralph A. Rivero, Michael N. Greco, and Bruce E. Maryanoff: *Equipment for the High-throughput Organic Synthesis of Chemical Libraries*, 1997, *A Practical Guide to Combinatorial Chemistry*, ACS); it is not only impossible to perform the whole steps of reaction automatically, but such automatic appliances are not commonly used because of it's extremely high price(R. N. Zuckermann et al.: *Int. J. Pept. Protein, Res.*, 40, 497 (1992); R. Frank et al.: *Tetrahedron*, 44,6031 (1988); *Automated Combinatorial Chemistry on Solid Phase*, Ontogen Corp.).

To produce groups of chemical compounds by combinatorial chemistry, it is required first to see if a reaction is successful in the liquid phase, and, if it is, next to try a reaction in the solid phase, and, if successful again, then to construct a library of the compounds. The constructed libraries are arbitrarily or selectively, wholly or partially, subjected to a quality control. A number of libraries had been constructed by way of above methods in early days, but nowadays approaches which lead to generate more focused libraries are used in general. But, specialized synthetic companies are still generating tens of thousands or hundreds of thousands of libraries from a same scaffold In these cases, a certain number of lead compounds for a desired target compound may be usually found within several months.

As mentioned above, synthetic apparatuses capable of synthesizing compounds automatically or semiautomatically may well be required when a large numbers of libraries arc to be generated, but also there's a case any special synthetic apparatus is not needed when only scores or hundreds of libraries are to be generated.

As a synthetic reaction vessel to solve the problems of synthetic apparatuses having vertical types of reaction vessels, "a boat type reaction vessel for synthesis of peptide or DNA" has been described in KP issuance No. patent 1997-4691. while this boat shaped vessel, having an inlet on the left side and an outlet on the right, both formed slantwise, has solved part of the problems of vertical types. But it still has got its own defects in that it is by the nature of its construction difficult to fix the reactors in a certain position, and further, it takes too much time in washing each of the plurality of boat shaped reactors which are required in multiplex synthesis such as libraries of chemical compounds by using a vacuum pump. Moreover, it is too much of a task to separate the final product in the each reactor, one by one, after completion of the reaction.

TECHNICAL FIELD OF INVENTION

Therefore, an objective of the present invention is to provide an organic synthetic reaction vessel, economical, efficient, and for wide-use, along with a block device to set it in, which has successfully solved such defects of the conventional automatic, semi-automatic, or boat-shaped reaction vessels by being easy to set up, convenient in use, free of friction on the resin during the reaction, and easy of washing the mixture and resin during the reaction.

Another objective of the present invention is to provide a method for conveniently and efficiently synthesizing chemical compounds or their libraries by the use of the said organic synthetic reaction vessel and its block device of the present invention.

To attain these objectives the present invention provides a reaction vessel for the solid phase organic synthesis having a filter and a block device capable of mounting these reaction vessels simultaneously.

The construction of the present invention is as follows. The reaction vessel (also used as "organic synthetic reaction vessel" herein) in the present invention relates to a reaction vessel in the form of a single hollow tube as a whole, comprising a horizontal part; a vertical part formed by bending upward from an end of the said horizontal part; an inlet formed by bending upward from the other end of the said horizontal part; an outlet formed by bending the upper part of the said vertical part in parallel with the said horizontal part in the opposite direction to the said inlet and engaged with a connection joint; and a filter mounted within one end of the said horizontal part or the said vertical part. Preferably, the said vertical part gradually tapers upward, i.e. getting narrower as it rises upward.

In another aspect of the present invention, the said block device is comprising:

a hexahedral frame, whose upper side is opened, and the front is capable of getting closed or opened, a block contacting with the inner face of the rear side and inner faces of both sides of the said frame without a gap and having a vacuum passage going through both sides of the said frame horizontally; a plurality of cock grooves formed in the upper part in a specific intervals and depth; connection joint insertion grooves formed in the front part in the same intervals with the said cock grooves so as to connect to the said cock grooves; a plurality of small vacuum tubes formed in the same intervals with the said cock grooves and connecting the said cock grooves to the said vacuum passage; and a plurality of sample outlets connecting the outer face of the rear side of the said fame to the said cock grooves;

a plurality of cocks having the connection joint insertion groove, the said small vacuum tube, and a first and a second passage connecting the said connection joint insertion groove and the said outlet respectively, and rotating after inserted into the said cock grooves without a gap;

a catch projection extending from the said vacuum passage in the outside of one side of the said hexahedral frame;

a catch groove capable of engaging closely with the said catch projection and stopper without a gap in the other side which is connected to the said catch projection by the vacuum passage.

In another preferred embodiment of the present invention, a cover having a hole capable of optionally blowing gases may be further attached to the upper face of the said frame.

In another preferred embodiment, the present invention includes a method for synthesizing chemical compounds and libraries such as peptides, oligonucleotides by using the said organic synthetic reaction vessel and block device.

The construction and functions of the present invention are described in detail as follows.

Figure 1:
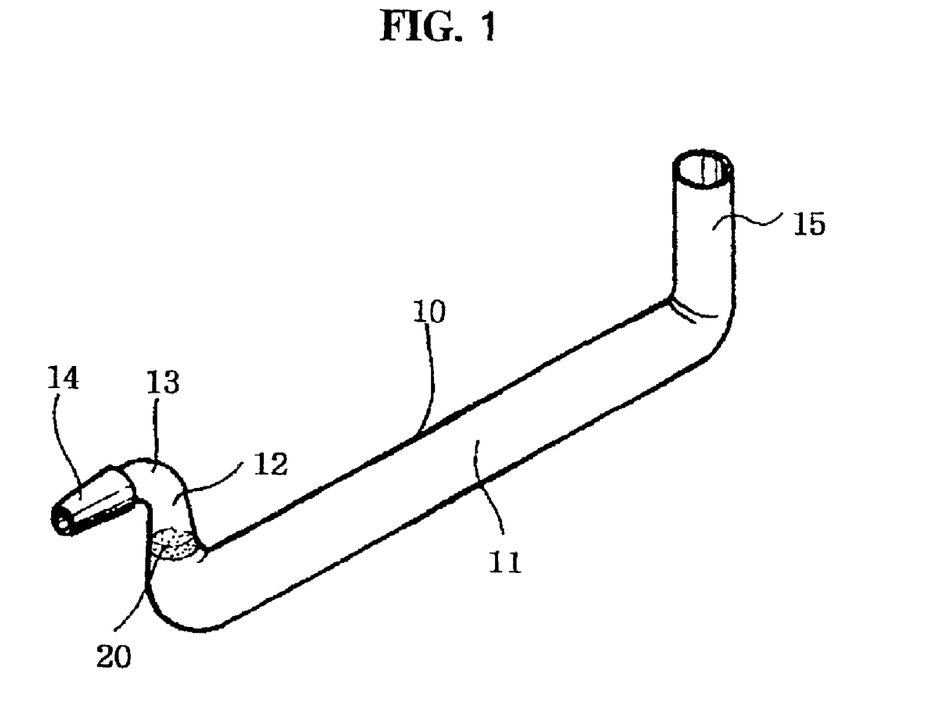
FIG. 1 is a perspective view of the organic synthetic reaction vessel of the present invention.

The said reaction vessel in the present invention is made of a hollow tube of glass or plastic material, etc., available at cheap prices on the market, including polypropylene, etc., inside which a filter of meshes finer than the resin (about 100–200 mesh) for synthesis is fitted at a position one eighth to one tenth of the said hollow tube, and the end part of the tube nearer to the fixed filter plate tapering and bending vertically upward next to get bent again horizontally and is terminated in a connection joint. The other end part of the tube is also bent vertically upward to serve as the inlet of samples or solvents. The thus constructed reaction vessel of the present invention is single hollow tube 10 as a whole, comprising a horizontal part 11; a vertical part 12 formed by bending upward from an end of the said horizontal part; an inlet 15 formed by bending upward from the other end of the said horizontal part; an outlet 13 formed by bending the upper part of the said vertical part in parallel with the said horizontal part in the opposite direction to the said inlet and engaged with a connection joint 14; and a filter 20 mounted within one end of the said horizontal part or the said vertical part. Preferably, the said vertical part gradually tapers upward, and the filter is resistant to an organic solvents.

These types of reaction vessels are convenient in comparison with the conventional vertical type reaction vessels in that there is no need to mount a gasket in every well because there may be not any chances the reaction solutions to leak. FIG. 1 illustrates the structure of the organic synthetic reaction vessel of the present invention.

Further, the present invention provides a block device capable of mounting the reaction vessels simultaneously and thereby conducting reactions stably, and allowing rapid and easy washing and recovery after the completion of the reaction.

i.e, the present invention is to simultaneously conduct reactions and remove the reagents and solvents in excess after completion of reaction by mounting several or scores of the reaction vessels into the block device of the present invention. It is to solve the conventional problems in the solid phase organic synthesis which needs to remove the reagents and solvents in excess at each stage of the reaction by way of using single vacuum passage.

Figure 2:
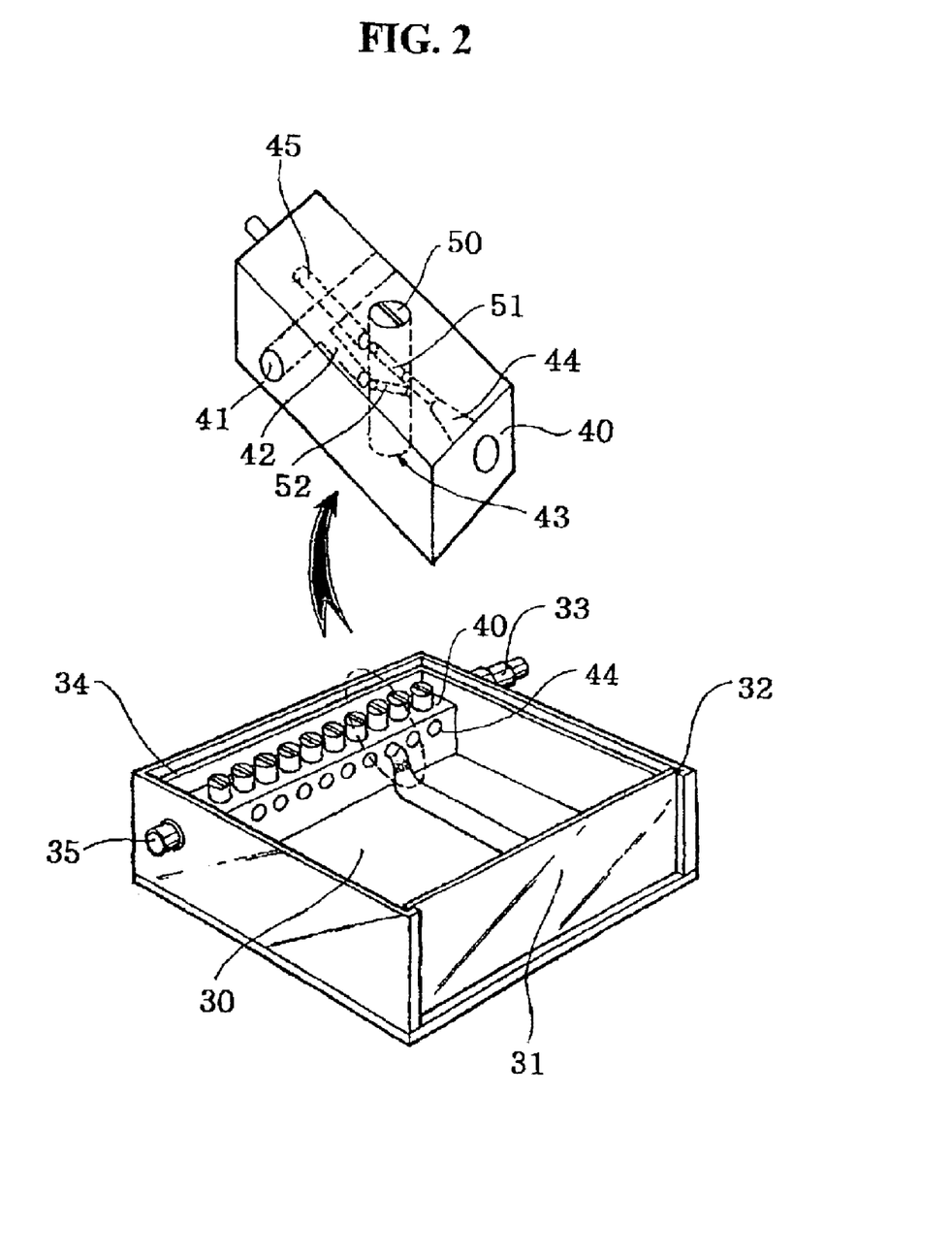
FIG. 2 is a perspective view illustrating the block device mounted with the reaction vessel for organic synthesis of the present invention and it's partial enlargement perspective view illustrating the internal structure.
Figure 3:
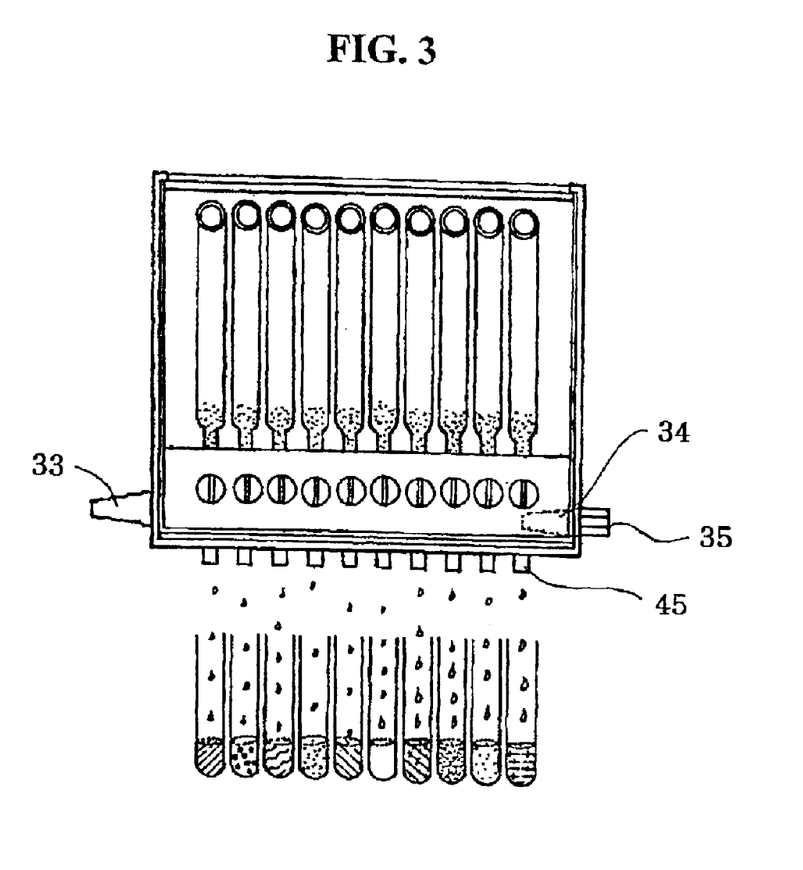
FIG. 3 illustrates a process obtaining final products after completing synthesis by using the reaction vessels and the block devices for the reaction vessels of the present invention.

FIG. 2. is a perspective view illustrating the whole structure of the block device of one embodiment of the present invention and partial enlargement illustrating the inside structure of a cock having the connection joint insertion groove, a small vacuum tube, and a first and a second passage connecting respectively to a connection joint insertion groove and die outlet. FIG. 3 illustrates a process of recovering final products after completing synthesis by using the reaction vessels and the block devices for the reaction vessels of the present invention.

FIG. 2 illustrates a reaction vessel mounted within a reaction vessel block device, and it is also possible to assemble an apparatus capable of obtaining large numbers of molecules simultaneously and easily by mounting reaction vessels within the block device as many as it is required and optionally connecting to the other reaction vessel block devices.

FIG. 3 illustrates a separation process of reaction products after completion of reaction by using a cock capable of selecting and controlling the vacuum passage and sample outlet which is mounted within the reaction vessel block device and thereby conducting resin removal reactions simultaneously without separating the reaction vessels.

A construction of one embodiment of the present invention, reaction vessel block device, will be described in reference to above mentioned Figures, comprising;

a hexahedral frame 30 whose upper side is opened and the front 31 is capable of getting closed or opened up and down slidingly along the guide groove 32 which is formed in the each of the inner face of the both sides;

a block 40 contacting with the inner face of the rear side and inner faces of the both sides of the said frame without a gap and having a vacuum passage 41 going through both sides of the said frame horizontally; a plurality of cock grooves 43 formed in the upper part in a specific intervals and depth; connection joint insertion grooves 44 formed in the front part in the same intervals with the said cock grooves so as to connect to the said cock grooves; a plurality of small vacuum tubes 42 formed in the same intervals with the said cock grooves and connecting the said cock grooves to the said vacuum passage; and a plurality of sample outlets 45 connecting the outer face of the rear side of the said frame to the said cock grooves;

a plurality of cocks 50 having the connection joint insertion groove 44, the said small vacuum tube 42, and a first passage 51 and a second passage 52 connecting the said connection joint insertion groove 44 and the said outlet 45 respectively, and rotating after inserted into the said cock grooves without a gap;

a catch projection 33 extending from the said vacuum passage in the outside of one side of the said hexahedral fame 30;

a catch groove 34 capable of engaging closely with the said catch projection or stopper 35 without a gap in the other side which is connected to the said catch projection 33 by the vacuum passage;

a cover in the upper face of the frame having a hole capable of blowing gases into and covering the frame.

In the said hexahedral frame, the front may either be formed into a sliding door capable of moving up and down along the guide groove as shown in the drawing or a door opening or shutting in the ordinary way, of pulling out or pushing back. This front may serve to keep the reaction vessels from getting themselves off the connection joint insertion grooves after they are mounted in them.

Further, a plurality of connection joint insertion grooves and a block device having the same number of small vacuum tubes, the same number of sample outlets, vacuum passage, connection joint insertion groove and the same numbers of cocks are mounted within the frame. The blocks are mounted by contacting closely with the inner face of the rear side and the each of the inner faces of the both sides of the frame without a gap. Inside the block, a vacuum passage is formed which is going through both sides of the frame horizontally and connected to a plurality of small vacuum tubes. Inside the block the connection joint insertion grooves, sample outlets and cock grooves are also formed.

Inside each of the cock grooves, a cock having two passages formed in the different directions are inserted tightly. During the reaction, each cock is closed, and after completing the reaction the cock is so turned as to get the connection joint insertion groove and the small vacuum tube to be connected via the first passage, and thereby allowing the reagents and washing buffer solution to be discharged rapidly by a vacuum. Further, when the reaction is fully completed, the synthesized products are discharged by breaking the chemical bonds between the resins and the synthesized products and then connecting the connection joint insertion grooves to the sample outlets via the second passage by turning the cocks.

Further, the cocks are formed in such a structure as each can individually be opened or closed.

Outside the vacuum passage, a catch projection is formed on one side and the catch groove is formed on the other side. The catch projection and the catch groove are formed so that they may be tightly connected, and thereby optionally connecting a plurality of block devices, processes such as reaction and washing etc. can be conducted simultaneously. When the processes such as reaction and washing etc. are conducted by using a single block device, a stopper tightly engaging with the catch groove is connected with the one end.

The solid phase synthesis reaction by using the reaction vessels and block device of the present invention is performed as follows.

First as many as required of the reaction vessels are mounted within the block device. it may be mounted simply by inserting the connection joints of the reaction vessels into the connection joint insertion grooves of the block. In the block device which may be mountable a specific number of reaction vessels, the catch projection and catch groove of the vacuum passage are formed on each side and thereby a plurality of block devices may be connected in parallel to each other by closely contacting and connecting the catch projection to catch groove in the other block device or vice verse.

Figure 4:
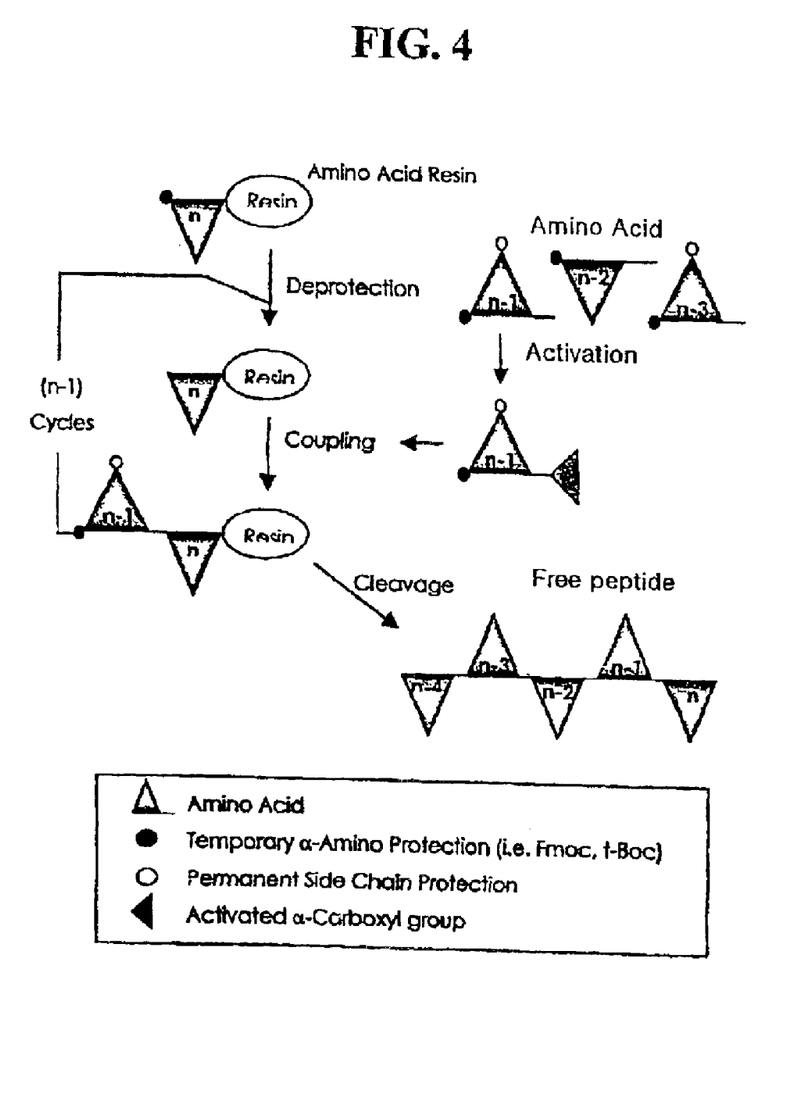
FIG. 4 illustrates a synthetic process for peptides by using solid phase resins.

Add resins into the reaction vessel and then add solutes which will be reacted with the resin in excess quantity and solvents into the reaction vessel containing resins, and then homogeneously mix the mixtures at the rotating speed of 150 to 300 rpm by using a Rocker. FIG. 4 illustrates how the mixture is homogeneously mixed.

After one synthetic step is completed, the reactants in excess are removed by opening the cock to connect the reaction vessel to the small vacuum tube through the first passage by making vacuous via vacuum passage and the apparatus is washed with buffer solution etc. and then a new synthetic step is conducted by closing the cock and adding new reactants into the reaction vessels through inlets, after completing the step, the reactants in excess are removed and the apparatus is washed with buffer solutions etc. as in above mentioned manner. The synthetic reaction is conducted by repeating the steps in this way.

Figure 5:
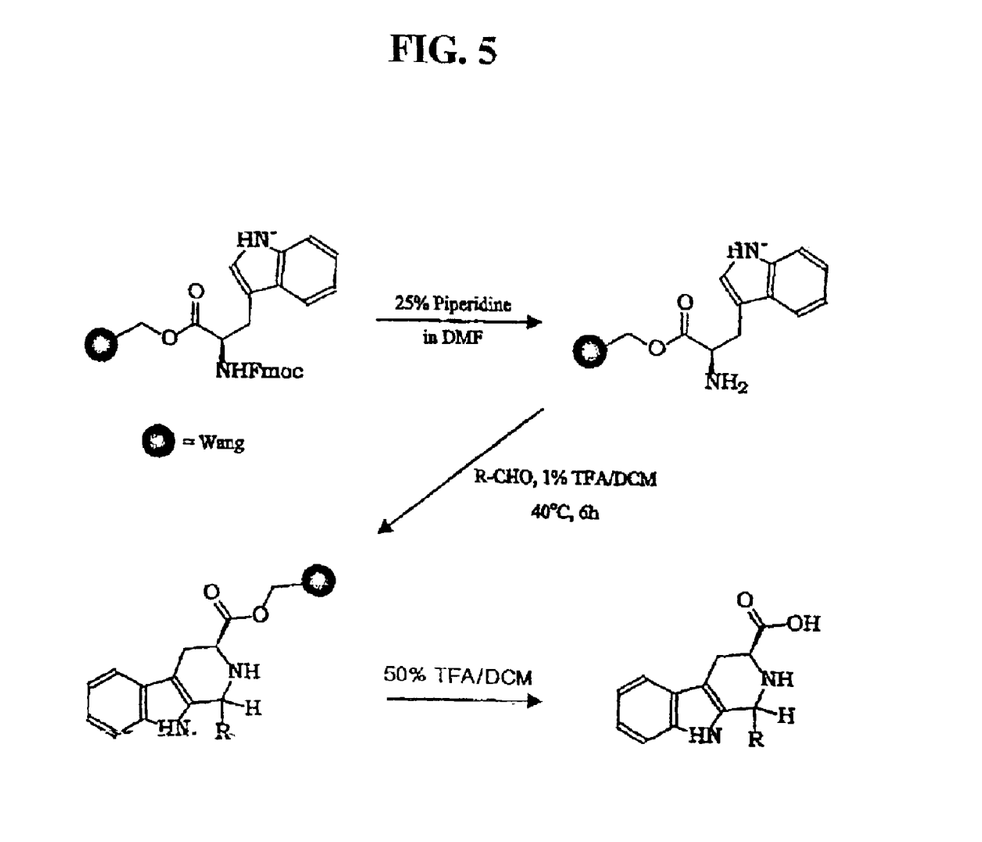
FIG. 5 illustrates a construction process for a library of chemical compounds through the Pictet-Spengler cyclization reaction by using solid phase synthesis method.

In case the reaction requires a steady maintenance of high or low temperature it may be possible to attach a heating plate capable of controlling temperatures at the bottom of the block device. Also, when the reaction should be conducted under the atmosphere of nitrogen or argon gases, the reaction is conducted while circulating the inert gases trough the hole in the cover of reaction vessel block device. After synthesizing the target molecules by repeatedly applying above methods, the final target molecules are separated from the resins. FIG. 5 illustrates the process separating the final products and the resins in the reaction vessels of the present invention. When the synthetic reaction is fully completed, the final products are discharged through the sample outlets by cleaving the chemical bonds between the resins and final products and by connecting the connection joint insertion groove to the sample outlets via the second passage by turning the cock.

As mentioned above, the reaction vessels and the block devices of the present invention are inexpensive and easy to manufacture, while their uses are also very simple and convenient so that anyone can easily perform the solid phase organic synthesis.

BRIEF DESCRIPTION OF THE SYMBOLS AND NUMBERS IN THE DRAWINGS

10: reaction vessel for organic synthesis
11: horizontal part
12: vertical part
13: outlet
14: connection joint
15: inlet
20: filter
30: frame
31: front
32: guide groove
33: catch projection
34: catch groove
35: stopper
40: block
41: vacuum passage
42: small vacuum tube
43: cock groove
44: insertion groove
45: sample outlet
50: cock
51: 1st passage
52: 2nd passage

BEST MODE FOR CARRYING OUT THE INVENTION

The present invention will be further described in detail through preferred embodiments, but these embodiments are only intended to clearly describe the invention, therefore, the spit and scope of the appended claims should not be limited to the description of the preferred embodiments herein.

Generally, to synthesize physiologically active materials, reagents such as Wang's resin, amino acid, piperidine, N-methylpyrrolidone and dicyclohexylcarbodiimide, etc. commonly available commercially are obtained and used as they were.

EXAMPLE 1

To conduct a solid phase synthetic reaction in each of the reaction vessel, 40 mg(loading level, 0.5 mmol/g), 40 μmol of Wang's resin whose alcohol group is substituted was prepared and 5 equivalents, 0.2 mmol of each of the amino acid composing the peptide sequences to be synthesized was added in each of the reaction vessels. And then the amino acid was coupled to the resins by way of ester bonds which is formed by condensing the hydroxyl groups of Wang's resin and the acid group of amino acid whose N-terminal is substituted with Fmoc. The amino acids and reagents in excess used were filtered and washed by filtering and washing the resins by using vacuum pumps which were attached to the vacuum passage. To add another amino acid to the amino acid covalently bonded to the resins, the N-terminal Fmoc group of amino acid covalently bonded to the resins was deprotected with 20% solutions of piperidine and the acid group of the amino acid to be added was activated, and amide bond was created by reacting the activated acid group of the amino acid to be added with the amine group of the N-terminal of the resins. Thus, the desired polypeptide was synthesized by coupling repeatedly other amino acids in the order of amino acid sequence of the polypeptide to be synthesized(FIG. 4). Then, at the original state of the reaction vessel assembly, the peptides were separated from the peptidyl resins by adding 1.0 ml of resin decoupling solutions in each of the reaction vessel.

A white solid precipitate was generated by adding 15 ml of diethylether into the separated peptide solutions. After washing the generated solid precipitate(peptide) with diethylether three to five times further, the generated solid precipitate was dried at room temperature. The synthetic yield and purity of the dried peptide analogs were confirmed and purified by using the reverse phase high performance chromatography(HPLC)(Table 1).

TABLE No. 1

| Number | amino acid sequence of the peptide | HPLC purity | Crude yield |
|---|---|---|---|
| 1 | SFGDRNKTSPNSFWS | 84% | 74 |
| 2 | FKKGSTYKRDELLHR | 87% | 77 |
| 3 | GNFRREPPYILNMCS | 90% | 82 |
| 4 | KKERCVHLQNSSGNT | 89% | 81 |
| 5 | ELYFPPHISAALRRR | 79% | 70 |
| 6 | SEHHIESKKLASRCK | 93% | 86 |
| 7 | IYRDCVNMMASSEDD | 94% | 83 |
| 8 | ASISEDDLKKECKAA | 88% | 80 |
| 9 | PSEDDEHISLLKGHK | 90% | 83 |
| 10 | KKKMCCLEKFGQWDF | 96% | 91 |

EXAMPLE 2

In conducting the Pictet-Spengler cyclization (Cox,. E. D; Cook, J. M. Chem. Rev., 1995, 95, 1797) reaction to synthesize tetrahydro-b-caxbline (THBC), one of the heterocyclic compounds, a library of chemical compounds was constructed by using solid phase synthetic method(FIG. 5). The aldehyde and Wang's resin used in the reaction herein were available on the commercial market, and they were used as they were.

To construct the library of above chemical compounds, 10 compounds having varying functional groups(R) respectively was synthesized by using the reaction vessels and the block device of the present invention as follows.

20 mg of N-a-Fmoc-tryptophan substituted Wang's resin (0.4 mmol/g) was added to the reaction vessel respectively and washed three times with 1.0 ml of dichloromethane. 5 equivalents of each of the 10 aldehyde derivatives was solubilized with 1 ml of dichloromethane trifluoroacetate solution and then added to the reaction vessels respectively.

The reaction vessel was introduced into the incubator at 40° C. and the reacton mixture was agitated for 6 hours with rotating speed of 600 rpm.

After completion of the reaction, the respective resins from the ten reaction mixtures was simultaneously filtered and washed with 5.0 ml of dichloromethane by using washing lines mounted on the block device. To separate the synthesized b-carbline compounds from the resins, the compounds were reacted with 1.0 ml of dichloromethane trifluoroacetate solutions for 30 minutes. The compounds separated from the resins were transferred into the test tube respectively and then dried after removing the solvents under vacuum conditions.

The yield and purity of the 10 kinds of the dried b-cabline compounds was confirmed by using reverse phase chromatography(Table 2).

| Number | Functional group (R) | Crude yield | HPLC purity |
|--------|---------------------|-------------|-------------|
| 1 | Ph— | 90% | 95 |
| 2 | 4-OMe—Ph— | 97% | 98 |
| 3 | 4-Cl—Ph— | 94% | 98 |
| 4 | 4-NO2-Ph— | 90% | 97 |
| 5 | CH3(CH2)3- | 83% | 98 |
| 6 | Ph—CH=CH— | 84% | 79 |
| 7 | 4-Pyr | 83% | 78 |
| 8 | 3-Pyr | 85% | 98 |
| 9 | 4-B(OH)2-Ph— | 78% | 98 |
| 10 | 4-OH—Ph | 93% | 95 |

As shown in Tables 1 and 2 the yield and purity obtained by using the reaction vessels and the block device at the present invention was relatively higher, in comparison with those obtained by using other synthetic apparatuses.

As above mentioned, according to the organic synthesis reaction vessels and block device of the present invention, it is convenient in assembly, introduction and washing of samples, and recovery of the final products.

Also, according to the organic synthesis reaction vessels and block device of the present invention, it is possible to conduct a multiplex synthesis reaction conveniently by remarkably reducing the time and efforts required in the multiplex synthesis reaction which uses a plurality of reaction vessels simultaneously.

What is claimed is:

1. An organic synthesis reaction vessel in the form of a single hollow tube as a whole, comprising;
   a horizontal part;
   a vertical part formed by bending upward from an end of the said horizontal part;
   an inlet formed by bending upward from the other end of the said horizontal part;
   an outlet formed by bending the upper part of the said vertical part in parallel with the said horizontal part in the opposite direction to the said inlet and engaged with a connection joint;
   and a filter mounted within one end of the said horizontal part or the said vertical part.

2. The organic synthesis reaction vessel of the claim 1 wherein the filter is a organic solvent resistant filter.

3. A block device for reaction vessels, comprising;
   a hexahedral frame whose front is capable of getting closed or opened;
   a block contacting with the inner face of the rear side and inner faces of both sides of the said frame without a gap and having a vacuum passage going through both sides of the said frame horizontally, a plurality of cock grooves formed in the upper part in a specific intervals and depth; connection joint insertion grooves formed in the front part in the same intervals with the said cock grooves so as to connect to the said cock grooves; a plurality of small vacuum tubes formed in the same intervals with the said cock grooves and connecting the said cock grooves and the said vacuum passage; and a plurality of sample outlets connecting the outer face of the rear side of the said frame to the said cock grooves;
   a plurality of cocks having the connection joint insertion groove, the said small vacuum tube, and a first and a second passage connecting the said connection joint insertion groove and the said outlet respectively, and rotating after inserted into the said cock grooves without a gap;
   a catch projection extending from the said vacuum passage in the outside of one side of the said hexahedral frame;
   a catch groove capable of closely engaging with the said catch projection and stopper without a gap in the other side which is connected to the said catch projection by the vacuum passage.

4. The block device for reaction vessels of the claim 3 wherein the fame further comprises a cover having a hole capable of blowing gases into in the upper face of the frame.

5. A method for synthesizing a compound or a library of compounds by using the organic synthesis reaction vessel of the claim 1 or 2 and the block device for reaction vessels of the claim 3 or 4.

6. The method of the claim 5 wherein the compound is a peptide.

7. The method of the claim 5 wherein the compound is a oligonucleotide.

* * * * *